United States Patent
Kyle et al.

(10) Patent No.: US 7,908,901 B2
(45) Date of Patent: Mar. 22, 2011

(54) COOLING APPARATUS FOR MICROWAVE CHROMATOGRAPHY

(75) Inventors: Kevin Kyle, Clute, TX (US); Larry Youngblood, Houston, TX (US); Michael King, Crosby, TX (US); Jan Vondras, Ostrov (CZ); Sean Rick, Cypress, TX (US)

(73) Assignee: Petroleum Analyzer Company, LP, San Antonio, TX (US)

( * ) Notice: Subject to any disclaimer, the term of this patent is extended or adjusted under 35 U.S.C. 154(b) by 540 days.

(21) Appl. No.: 11/834,509

(22) Filed: Aug. 6, 2007

(65) Prior Publication Data

US 2009/0049888 A1    Feb. 26, 2009

(51) Int. Cl.
*G01N 30/00* (2006.01)
(52) U.S. Cl. .................................... 73/23.35
(58) Field of Classification Search ............ 73/23.35; 219/757, 678
See application file for complete search history.

(56) References Cited

U.S. PATENT DOCUMENTS

| | | | |
|---|---|---|---|
| 3,169,389 A | 2/1965 | Green, Jr. et al. | |
| 3,232,093 A | 2/1966 | Burow et al. | |
| 3,516,771 A | 6/1970 | Rendina | |
| 3,527,567 A | 9/1970 | Philyaw et al. | |
| 3,676,058 A * | 7/1972 | Gray | 422/21 |
| 4,204,423 A | 5/1980 | Jordan | |
| 5,005,339 A | 4/1991 | Capawana | |
| 5,370,529 A | 12/1994 | Lu et al. | |
| 5,939,614 A * | 8/1999 | Walters et al. | 73/23.39 |
| 6,029,498 A * | 2/2000 | Walters et al. | 73/23.39 |
| 6,093,921 A * | 7/2000 | Gaisford et al. | 219/748 |
| 6,155,212 A | 12/2000 | McAlister | |
| 6,157,015 A * | 12/2000 | Gaisford et al. | 219/748 |
| 6,182,504 B1 | 2/2001 | Gaisford | |
| 6,316,759 B2 * | 11/2001 | Gaisford et al. | 219/748 |
| 6,514,316 B1 | 2/2003 | Gaisford et al. | |
| 6,762,834 B2 | 7/2004 | Komatani et al. | |
| 6,867,400 B2 * | 3/2005 | Collins et al. | 219/687 |
| 7,291,203 B2 * | 11/2007 | Crnko et al. | 95/87 |
| 2005/0133498 A1 * | 6/2005 | Collins et al. | 219/687 |

* cited by examiner

*Primary Examiner* — Hezron Williams
*Assistant Examiner* — Rodney T Frank
(74) *Attorney, Agent, or Firm* — Gunn, Lee & Cave, P.C.

(57) ABSTRACT

A cooling apparatus for a radiant energy heated oven is disclosed, where the cooling apparatus cools the oven by directing a flow of coolant through a chamber in thermal communication with the oven resulting in sub-ambient cooling, sub-ambient holds, and in chromatography instruments, higher sample throughput by reducing cycle time or column cool down time.

25 Claims, 9 Drawing Sheets

COOLING APPARATUS FOR MICROWAVE CHROMATOGRAPHY

BACKGROUND OF THE INVENTION

1. Field of the Invention

The present invention relates to a cooling system or apparatus in the field of liquid and gas chromatography instruments heated by radiant energy such as microwave or radiowave radiant energy and to methods for making and using same.

More particularly, the present invention relates to a cooling system or apparatus in the field of liquid and gas chromatography instruments heated by radiant energy such as microwave or radiowave radiant energy and to methods for making and using same. The cooling system includes a cooling apparatus having an coolant inlet and a coolant outlet, a supply of a coolant, a conduit connecting the cooling apparatus to the coolant supply, where the cooling system is adapted to permit lower start temperatures and faster post run cool down resulting in faster cycling between samples or shorter sample cycle times. The present invention also relates to a microwave oven for use in liquid and gas chromatography instruments including a microwave oven having such a cooling apparatus and to methods for making and using same.

2. Description of the Related Art

Gas and liquid chromatography are physical methods for the separation, identification, and quantification of chemical compounds. These methods are used extensively for applications that include the measurement of product purity in analytical chemistry, the determination of environmental contamination, the characterization of natural substances, and the development of pharmaceuticals.

The fundamental methods used in gas and liquid chromatography instruments to separate chemical constituents are similar. A sample mixture is injected into a flowing neutral carrier stream and the combination then flows through a tube or chromatographic column. The inner surface of the column is coated or the tube is packed with a material called the stationary phase. As the sample mixture and carrier stream flow through the column, the components within the mixture are retained by the stationary phase to a greater or lesser degree depending on the relative volatility (in the case of gas chromatography) or the relative solubility (in the case of liquid chromatography) of the individual components and/or on their respective affinities for the stationary phase. When the individual mixture components are released into the carrier stream by the stationary phase, they are swept towards the column outlet. As the combined flow exits the column outlet, the flow is forwarded to a detector, where the separated components are detected and measured. Different chemical components or compounds in the sample are retained for different times by the stationary phase or spend different amounts of time in the moving phase. By measuring the retention times, the specific compounds or components in the sample can be identified. The relative concentration of the components compounds is determined by comparing peak amplitudes measured with the detector for each compound or component in the sample. The peak amplitude are generally compared to peak heights for that component of know concentrations of the component or are derived from instrument calibration.

The primary difference between gas chromatography (GC) and liquid chromatography (LC) is the mode of separation. In gas chromatography, the sample is volatilized and propelled down the analytical column by a moving stream of gas. In liquid chromatography, the sample is dissolved and propelled down the analytical column in a moving stream of liquid. Another difference between gas and liquid chromatography is that the columns used in liquid chromatography have stationary phases that fill or are packed into the tube; while those used in gas chromatography can be packed, but generally the stationary phase is coated or bonded to the interior wall, instead.

GC and LC measurements are facilitated by the application of heat to the chromatographic column to change its temperature. The use of a heated column oven in gas chromatographic systems greatly increases the number of compounds that can be analyzed and speeds up the time required for each analysis by increasing the volatility of higher molecular weight compounds. Heating an LC column affects the relative solubility of the mixture's components in the two phases and can enhance the separation as well as improve the repeatability of the elution times of the component chemicals.

Many methods have been described for heating chromatographic columns. The simplest and most commonly used method utilizes resistive heating elements to heat air which is in turn circulated through an insulated oven in which the column is placed. For example, U.S. Pat. No. 3,527,567 to Philyaw et al. describes a GC oven heated with resistive elements.

The resistive element heating method has several limitations. To achieve even heating of the column, a large volume of air is rapidly circulated around the chromatographic column. In addition to heating the column, the air heats the oven itself. Because the thermal mass of the oven is much larger than that of the column, the rate at which the column can be heated is commensurately reduced. A related problem is cooling time. After heating the oven to a high temperature during an analysis, it takes significantly longer to cool the oven plus the column to their initial temperature so that the next sample may be analyzed than it would to cool the column alone. Together, these limitations reduce the throughput of the chromatography instruments.

Attempts to localize the resistive heat element onto the column itself so as to reduce or eliminate peripheral heating of the "oven" are described in U.S. Pat. No. 3,169,389 to Green et al., U.S. Pat. No. 3,232,093 to Burow et al., and in U.S. Pat. No. 5,005,399 to Holtzclaw et al. Each of these patents describe methods for directly wrapping or cladding the chromatographic column with a resistive heating element. Methods are also described for positioning the resulting metal clad column adjacent to a cooling source to decrease cooling times. This method of heating can be difficult to implement in practice because of uneven heating of the column due to local hot or cold spots in the resistive heating element surrounding the column. Uneven heating of the column in turn compromises the quality of the analysis.

Yet another limitation of all resistively heated chromatographic devices is that if operated improperly, they can be driven to temperatures higher than the maximum tolerated by a given column resulting in damage to or destruction of the column.

An alternative method for heating chromatographic columns is microwave heating as described in U.S. Pat. No. 4,204,423 or radio frequency heating described in U.S. Pat. No. 3,023,835. Additional background information on microwave heating instruments can be found in U.S. Pat. Nos. 6,514,316, 6,316,759, 6,182,504, 6,093,921, 6,029,498, and 5,939,614, incorporated herein by reference.

Although the microwave heated chromatography instruments have been disclosed, these units are not well equipped for low temperature starts or for fast sample cycling. Thus, there is a need in the art for microwave heated chromatography instruments including a cooling apparatus that permits

SUMMARY OF THE INVENTION

The present invention provides a cooling apparatus for a radiant energy heated chromatography oven, such as a microwave or radiowave oven, including a coolant chamber, in thermal contact with a radiant energy heated oven, a coolant inlet and a coolant outlet, where the inlet directs coolant into the chamber and the outlet directs spent coolant out of the member. The apparatus can include a closed-loop coolant assembly, where the spent coolant is returned to the coolant supply or reservoir. The radiant energy heated oven includes a chromatography column and is designed to heat the column to a desired temperature at a desired rate or to heat the column according to an temperature programmed heating profile. The cooling apparatus is designed to decrease the sample cycle time of an analytical instrument including such a cooled radiant energy heated oven. In certain embodiments, the cooling member includes a radiator with or without radiant fins, where the radiator is in direct thermal contact with the oven. The radiator and/or fins are designed to radiate heat away from the oven and the coolant is designed to absorb the heat from the radiator and/or fins resulting in cooling of the oven, rapid and/or controlled. In other embodiments, the cooling chamber comprises a flow channel associated with a top or bottom of the oven with or without a radiator, where the coolant flows through the channel resulting in oven cooling. Of course, the rate of cooling depends on the temperature of the coolant, the flow rate of the coolant, and the material out of which the radiator or flow chamber is made. By adjusting the coolant temperature, flow rate and material, the cooling apparatus can cool the oven at a desired and controlled rate. The cooling can also be used to hold the oven at a sub-ambient temperature at cycle start or during an analytical protocol. The cooling can be used for decreasing sample cycle times, i.e., the time between sample runs.

The present invention also provides a radiant energy or light heated oven apparatus for use in chromatography instruments including a housing having a radiant energy or light heated oven including a chromatographic column and cooling apparatus. In certain embodiments, the light or radiant energy is microwave radiation, while in other embodiments, the light or radiant energy is radiowave radiation. Of course, any frequency of light can be used provided that the light results in column heating in a controlled and repeatable manner. The cooling apparatus includes a coolant chamber, in thermal contact with the oven, a coolant inlet designed to direct coolant into the chamber and a coolant outlet designed to direct spent coolant out of the chamber. The apparatus can include a closed-loop coolant assembly, where the spent coolant is returned to the coolant supply or reservoir. The radiant energy heated oven includes a chromatography column and is designed to heat the column to a desired temperature at a desired rate or to heat the column according to an temperature programmed profile. The cooling apparatus is designed to decrease the sample cycle time of an analytical instrument including such a cooled radiant energy heated oven. In certain embodiments, the cooling member includes a radiator with or without radiant fins, where the radiator is in direct thermal contact with the oven. The radiator and/or fins are designed to radiate heat away from the oven and the coolant is designed to absorb the heat from the radiator and/or fins resulting in cooling of the oven, rapid and/or controlled. In other embodiments, the cooling chamber comprises a flow channel associated with a top or bottom of the oven with or without a radiator, where the coolant flows through the channel resulting in oven cooling. Of course, the rate of cooling depends on the temperature of the coolant, the flow rate of the coolant, and the material out of which the radiator or flow chamber is made. By adjusting the coolant temperature, flow rate and material, the cooling apparatus can cool the oven at a desired and controlled rate. The cooling can also be used to hold the oven at a sub-ambient temperature at cycle start or during an analytical protocol. The cooling can be used for decreasing sample cycle times, i.e., the time between sample runs. The cooling apparatus also includes a vortex cooler including a vortex inlet and a vortex outlet. The vortex outlet is connected to or integral with the coolant inlet and the vortex inlet is connect to a coolant supply. The cooling apparatus can also include flow controllers controlling an amount of coolant entering the chamber and an amount of coolant being feed to the vortex cooler.

The present invention also provides a light heated chromatography instrument including a sample delivery assembly. The instrument also includes a light heated oven apparatus of this invention. In certain embodiments, the light is microwave radiation, while in other embodiments, the light is radiowave radiation. The instrument also includes a detector/analyzer assembly. The instrument may also include oxidation subassemblies and/or reduction subassemblies.

The present invention also provides a method for cooling a light heated chromatography oven including the step of directing a coolant stream from a vortex cooler into a cooling chamber having a surface in thermal contact with the oven, where the chamber can comprise a flow channel or include a heat sink or radiator. In certain embodiments, the radiator can include fins. The coolant is supplied to the chamber at a rate and at a temperature sufficient to lower start temperatures and/or reduce cycle time, i.e., reduce a cool down time between sample runs.

The present invention also provides a method for performing chromatographic analyses including the step of providing an instrument of this invention. The method also includes the step of injecting a sample from a sample delivery system into the chromatographic column in a heating zone of a light heated oven apparatus. The method may also include cooling the oven to a sub-ambient start temperature. The method may also include the step of maintaining the sub-ambient temperature or a different sub-ambient temperature for a first time period after the injection step, but prior to the heating step. The method also includes the step of heating the column under conditions to affect a given separation of the components in the sample. After separation, the sample components can be forwarded to the detector/analyzer assembly. The method may also include the steps of oxidizing the sample components in an oxidation subassembly and/or reducing the sample components in a reduction subassembly prior to forwarding the resulting oxidized, reduced, or oxidized and reduced components to the detector/analyzer assembly. After forwarding the sample components to the detector/analyzer assembly, the oven is cooled using the cooling assembly to shorten a duration between subsequent sample injections, i.e., to increase a number of samples that can be processed in a given period of time or to decrease the instrument cycle time.

DEFINITIONS USED IN THE INVENTION

The term "temperature programmed heating profile" means a chromatography heating profile designed to achieve a desired analytical separation of components of a sample. In certain embodiments, the profiles is designed to maximize component separation. Profiles generally including at least one temperature ramp, positive or negative. The profiles can including one or a plurality of temperature holds. In certain embodiments, the temperature profile can include a sub-ambient start temperature, a sub-ambient hold temperature, or both. In other embodiments, the temperature profile can include an ambient start temperature, an ambient temperature hold or both. In other embodiments, the temperature profile can include an elevated start temperature, an elevated temperature hold or both. Thus, the profile can include a combination of start temperatures, holds, and negative and/or positive temperature ramps.

The term "positive temperature ramp" means changing a temperature from a lower temperature to a higher temperature at a desired rate. The rate can be single valued or complex meaning that the temperature can be increase at a linear rate, a combination of linear rates or a non-linear rate, where the rate is designed to achieve a given component separation.

The term "negative temperature ramp" means changing a temperature from a higher temperature to a lower temperature at a desired rate. The rate can be single valued or complex meaning that the temperature can be increase at a linear rate, a combination of linear rates or a non-linear rate, where the rate is designed to achieve a given component separation.

The term "hold" means that the column is heated to a desired temperature and held at that temperature for a desired period of time. Each hold can be held for a different period of time, where the hold times are designed to achieve a given component separation.

BRIEF DESCRIPTION OF THE DRAWINGS

The invention can be better understood with reference to the following detailed description together with the appended illustrative drawings in which like elements are numbered the same:

FIG. 7B depicts a top view of another embodiments of a microwave heated oven apparatus including a cooling system of this invention.

DETAILED DESCRIPTION OF THE INVENTION

Figure 1:
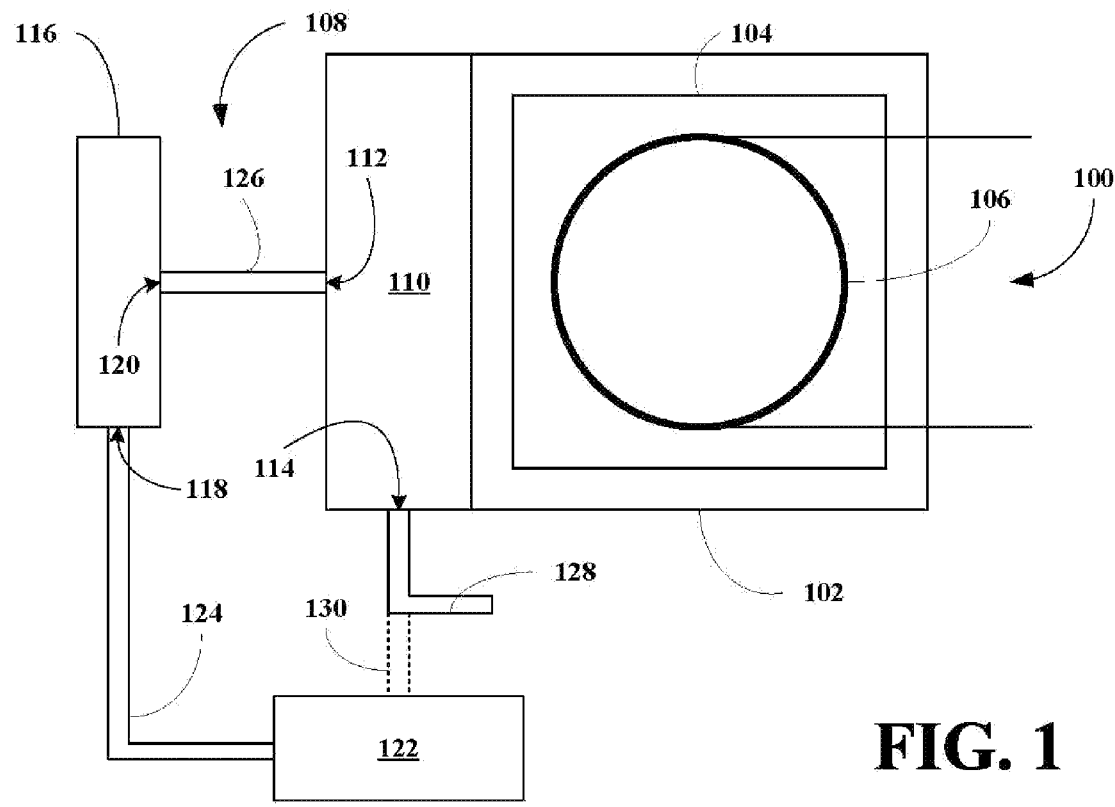
FIG. 1 depict a top view a generalized embodiment of a microwave oven apparatus including a cooling system of this invention.

The inventors have found that a microwave oven can be constructed with a cooling system making sub-ambient start temperatures and faster cycle times possible in microwave heated GC and LC instruments or to hold the column at a sub-ambient temperature during a microwave heated GC and LC instrument analysis. The inventors note that a key variable operators of chromatography instruments utilize in GC or LC analyses is the start temperature of the sample upon being introduced into the chromatographic column. Generally, a lower start temperature yields superior separation of low boiling components such as so-called light hydrocarbons. In practice, many operators resort to cooling the column with liquid nitrogen in order to achieve a low start temperature. In a microwave heated unit, due to the complicated nature of the thermal system, a number of constraints exist for cooling. The cooling system must be able to cool an environment around the microwave oven without disturbing the heated zones of the oven. The inventors have found that an effective and efficient cooling apparatus for a microwave oven can be constructed using a vortex cooled gas such as an inert gas, air, nitrogen or mixtures or combinations thereof. A fully pressurized vortex cooler provides sufficient cooled or cold coolant flow to keep a microwave heated analytical chromatographic column chamber at a desired sub ambient temperature. In certain applications, the sub ambient temperature is about 10° C. The inventors have also found that sub-ambient start temperatures make it easier for the heated zones to compensate and maintain their own temperature set points, with the oven body coming to equilibrium at or near the new ambient conditions. This effect translates into lower start of run temperature capabilities. The inventors have also found that cooling a microwave chamber give rises to a second and equally important benefit. Because the cooling apparatus forces coolant, a cooling fluid, across a heat sink on the back of or associated with the microwave oven, a much greater heat flux out can be used than would be possible with ambient temperature gas. The inventors have found that both benefits also serve to greatly reduce the cool down time or cycle time between runs and to assure that the system will be able to come back to its start of run temperature with greater repeatability. Thus, the present invention affords both benefits: lower start of run temperatures and faster cool down times or faster sample cycle times—reduced time between sample injections.

Suitable Reagents and Devices

Suitable coolants include, without limitation, gas and liquid coolants or mixtures or combinations thereof. Exemplary gas coolants include air, He, Ne, Ar, Xe, Kr, oxygen, nitrogen, $CO_2$, CO, ammonia, hydrocarbons, such as methane, ethane, propane, butane, or mixtures or combinations thereof. Exemplary liquids include water, liquid $CO_2$, liquid nitrogen, chlorocarbons, fluorochlorocarbons and other refrigerants, and mixtures thereof.

Suitable coolers include, without limitation, any refrigeration system of cooling a fluid, be it gas or liquid or a combination thereof. Exemplary gas coolers include Vortex® type coolers, liquidified gas coolers which provide a cooled stream of a gas, or any other type of gas refrigeration system. Exemplary liquid coolers include, without limitation, liquidified gas refrigeration and circulation system, liquid refrigeration and circulation system or the other similar refrigeration and circulation systems.

A General Cooling System Embodiment

Referring now to FIG. 1, a generalized embodiment of a cooled microwave oven apparatus of this invention, generally 100, is shown to include a housing 102. The housing 102 includes a microwave heated zone 104 including a chromatographic column 106. The housing 102 also includes a cooling system 108. The cooling system 108 includes a cooling chamber 110 having a chamber inlet 112 and a chamber outlet 114. The cooling system 108 also includes a vortex cooler 116 having a coolant inlet 118 and a cooled coolant outlet 120, where the coolant inlet 118 is connected to a source of a coolant or coolant reservoir 122 via a coolant conduit 124 and the cooled coolant outlet 120 is connected to the chamber inlet 112 via a cooled coolant conduit 126. The cooled coolant passes through the chamber 110 removing heat from the heated zone 104. The chamber outlet 114 is connected to an exhaust conduit 128. The chamber outlet 114 can also be connected to the coolant reservoir 122 for recycling of coolant is the coolant is to be recycled via a recycle conduit 130.

Cooling System Embodiments with Radiators

Figure 2:
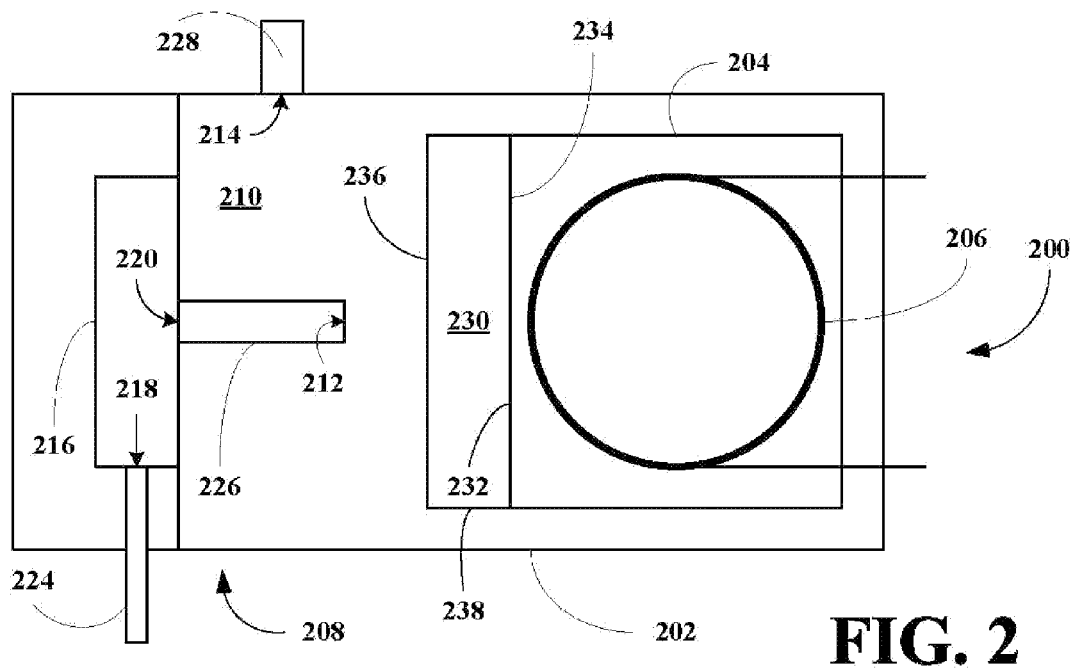
FIG. 2 depict a top view another embodiment of a microwave oven apparatus including a cooling system of this invention having a radiator or heat sink.

Referring now to FIG. 2, an embodiment of a cooled microwave oven apparatus of this invention, generally 200, is shown to include a housing 202. The housing 202 includes a microwave heated zone 204 including a chromatographic column 206. The housing 202 also includes a cooling system 208. The cooling system 208 includes a cooling chamber 210 having a chamber inlet 212 and a chamber outlet 214. The cooling system 208 also includes a vortex cooler 216 having a coolant inlet 218 and a cooled coolant outlet 220, where the coolant inlet 218 is connected to a source of a coolant or coolant reservoir (not shown) via a coolant conduit 224 and the cooled coolant outlet 220 is connected to the chamber inlet 212 via a cooled coolant conduit 226. The chamber outlet 214 is connected to an exhaust conduit 228. The cooling system 208 also includes a radiator or heat sink 230 having a back side or face 232 in thermal contact with the heated zone 204 along an edge 234 thereof and a front face 236 and sides 238. The front face 236 and sides 238 are exposed to the coolant passing through the chamber 210 resulting in thermal energy being absorbed by the coolant from the front face 236 and sides 238 of the heat sink or radiator 230.

Figure 3A:
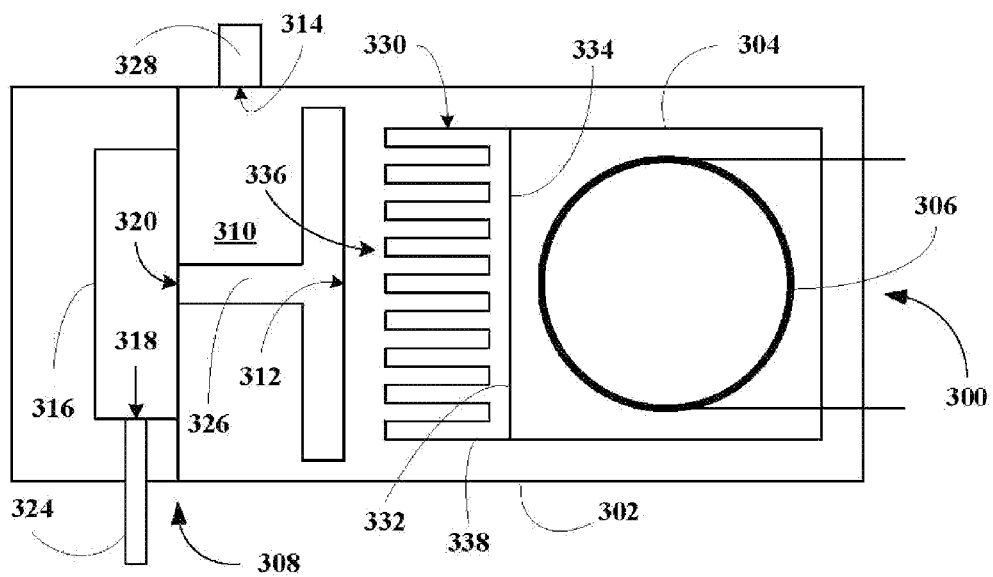
FIG. 3A depict a top view of another embodiments of a microwave heated oven apparatus including a cooling system of this invention having a radiator or heat sink.

Referring now to FIG. 3A, another embodiment of a cooled microwave oven apparatus of this invention, generally 300, is shown to include a housing 302. The housing 302 includes a microwave heated zone 304 including a chromatographic column 306. The housing 302 also includes a cooling system 308. The cooling system 308 includes a cooling chamber 310 having a chamber inlet 312 and a chamber outlet 314. The cooling system 308 also includes a vortex cooler 316 having a coolant inlet 318 and a cooled coolant outlet 320, where the coolant inlet 318 is connected to a source of a coolant or coolant reservoir (not shown) via a coolant conduit 324 and the cooled coolant outlet 320 is connected to the chamber inlet 312 via a cooled coolant conduit 326. The chamber outlet 314 is connected to an exhaust conduit 328. The cooling system 308 also includes a radiator or heat sink 330 having a back side or face 332 in thermal contact with the heated zone 304 along an edge 334 thereof and a front face 336 and sides 338. The front face 336 and sides 338 are exposed to the coolant passing through the chamber 310 resulting in thermal energy being absorbed by the coolant from the front face 336 and sides 338 of the heat sink or radiator 330.

Figure 3B:
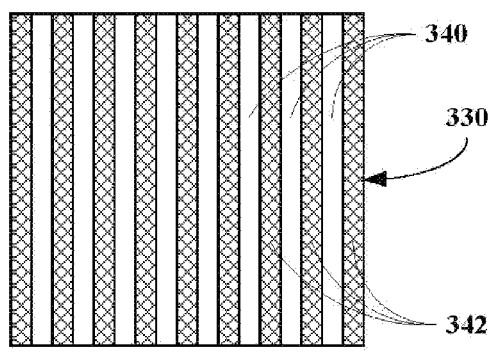
FIG. 3B depict a front view of the heat sink of FIG. 3A.

Referring now to FIG. 3B, a front view the radiator or heat sink 330 is shown to include fins 340 and valleys 342 designed to increase a surface area over which the coolant exiting the outlet 314 flows to improve cooling of the heated zone 304.

Figure 3C:
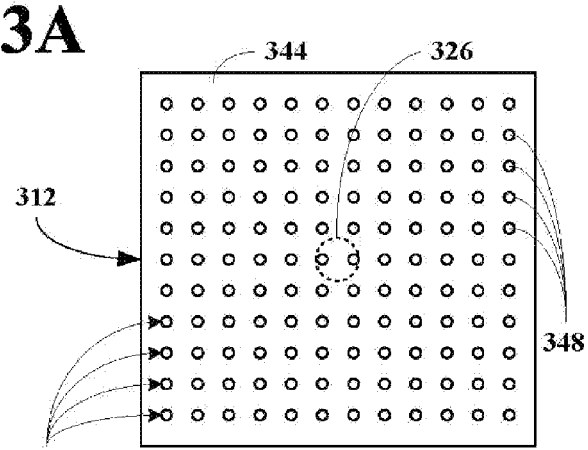
FIG. 3C depict a front view of a first embodiment of the cooler outlet of FIG. 3A.

Referring now to FIG. 3C, a front view a first embodiment of the chamber inlet 312 is shown connected to the cooled coolant conduit 326 and includes a front plate 344. The front plate 344 includes aligned rows 346 of apertures 348, where the apertures 348 are designed to more uniformly direct the coolant flows onto heat sink 330.

Figure 3D:
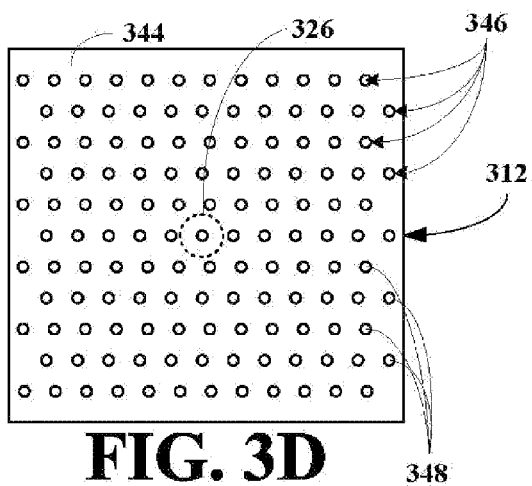
FIG. 3D depict a front view of a second embodiment of the cooler outlet of FIG. 3A.

Referring now to FIG. 3D, a front view a second embodiment of the chamber inlet 312 is shown connected to the cooled coolant conduit 326 and includes a front plate 344. The front plate 344 includes aligned rows 346 of apertures 348, where the apertures 348 are designed to more uniformly direct the coolant flows onto heat sink 330.

Figure 3E:
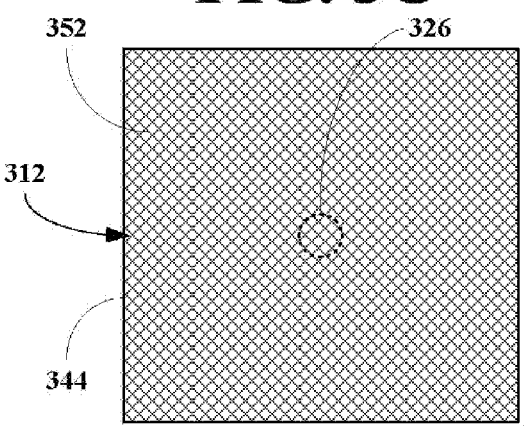
FIG. 3E depict a front view of a third embodiment of the cooler outlet of FIG. 3A.

Referring now to FIG. 3E, a front view a third embodiment of the chamber inlet 312 is shown connected to the cooled coolant conduit 326 and includes a front plate 344. The front plate 344 includes a screen 352, where the screen 352 is designed to more uniformly direct the coolant flows onto heat sink 330.

Figure 3F:
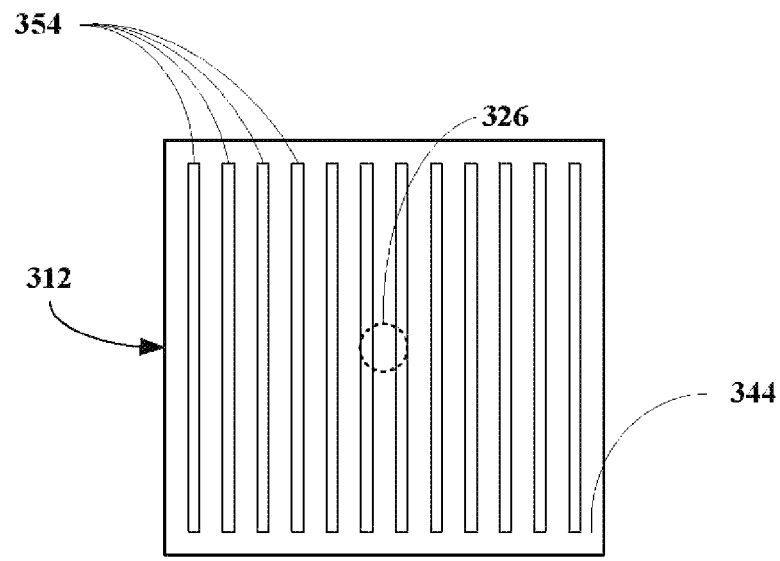
FIG. 3F depict a front view of a fourth embodiment of the cooler outlet of FIG. 3A.

Referring now to FIG. 3F, a front view a fourth embodiment of the chamber inlet 312 is shown connected to the cooled coolant conduit 326 and includes a front plate 344. The front plate 344 includes a plurality of slots 354, where the slots 354 is designed to more uniformly direct the coolant flows onto heat sink 330.

Figure 3G:
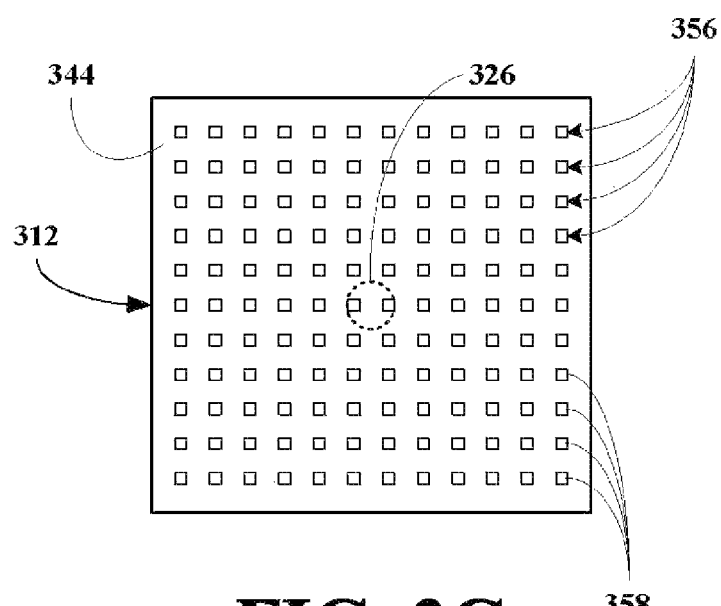
FIG. 3G depict a front view of a fourth embodiment of the cooler outlet of FIG. 3A.

Referring now to FIG. 3G, a front view a fifth embodiment of the chamber inlet 312 is shown connected to the cooled coolant conduit 326 and including a front plate 344. The front plate 346 includes aligned rows 356 of square apertures 358, where the apertures 358 are designed to more uniformly direct the coolant flows onto heat sink 330.

Figure 4A:
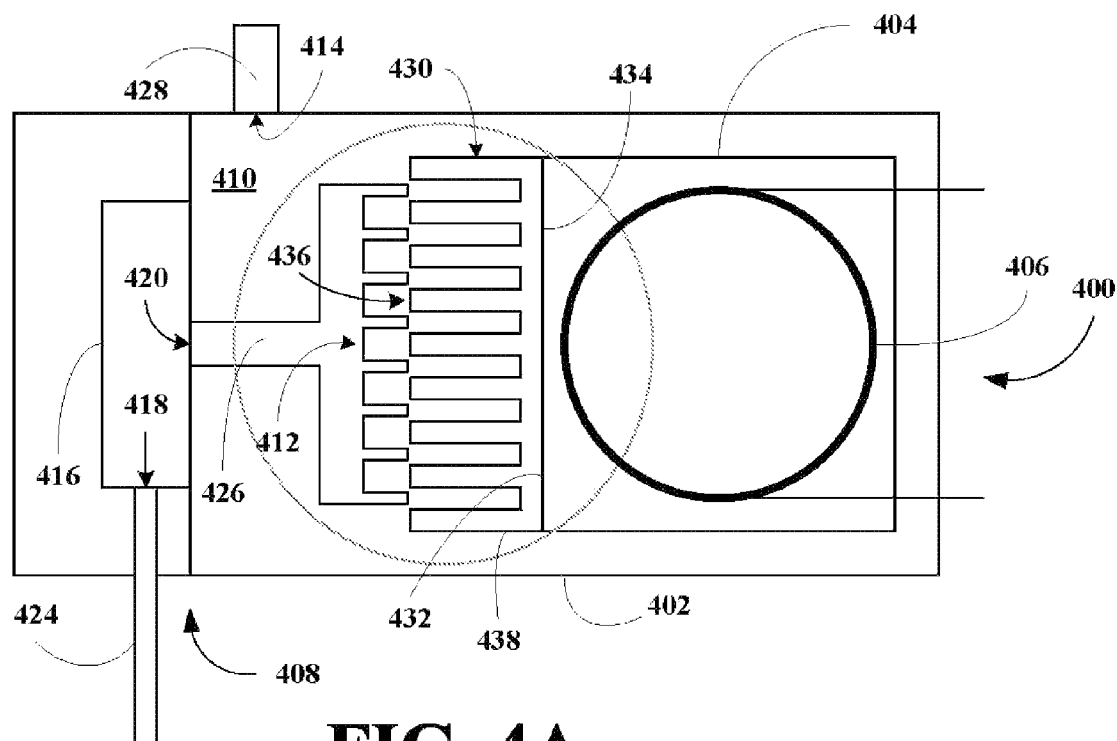
FIG. 4A depict a top view of another embodiments of a microwave heated oven apparatus of this invention including a cooling system.

Referring now to FIG. 4A, another embodiment of a cooled microwave oven apparatus of this invention, generally 400, is shown to include a housing 402. The housing 402 includes a microwave heated zone 404 including a chromatographic column 406. The housing 402 also includes a cooling system 408. The cooling system 408 includes a cooling chamber 410 having a chamber inlet 412 and a chamber outlet 414. The cooling system 408 also includes a vortex cooler 416 having a coolant inlet 418 and a cooled coolant outlet 420, where the coolant inlet 418 is connected to a source of a coolant or coolant reservoir (not shown) via a coolant conduit 424 and the cooled coolant outlet 420 is connected to the chamber inlet 412 via a cooled coolant conduit 426. The chamber outlet 414 is connected to an exhaust conduit 428. The cooling system 408 also includes a radiator or heat sink 430 having a back side or face 432 in thermal contact with the heated zone 404 along an edge 434 thereof and a front face 436 and sides 438. The front face 436 and sides 438 are exposed to the coolant passing through the chamber 410 resulting in thermal energy being absorbed by the coolant from the front face 436 and sides 438 of the heat sink or radiator 430.

Figure 4B:
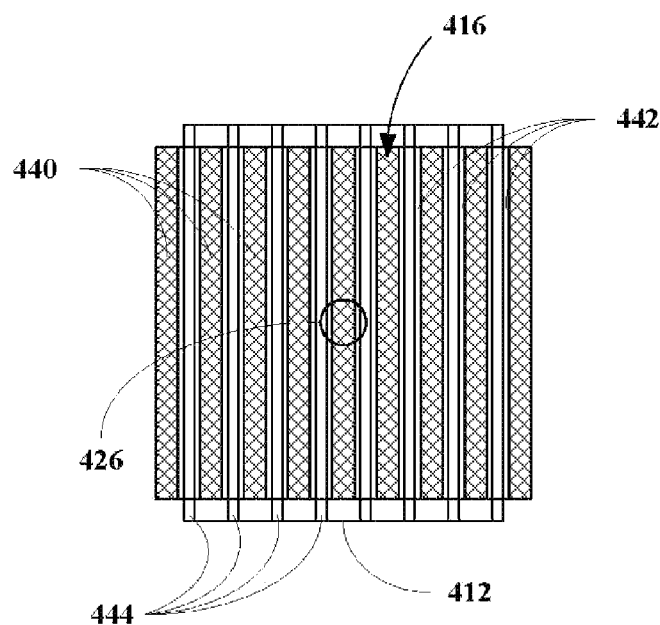
FIG. 4B depict an expanded view of the embodiment of FIG. 4A for the oval shaped region of FIG. 4A.

Referring now to FIG. 4B, a view looking down the cooled coolant conduit 426 in transparency at the heat sink 430. The heat sink 430 includes fins 440 and valleys 442 designed to increase a surface area over which the coolant exiting the chamber inlet 412 flows to improve cooling of the heated zone 404. The chamber inlet 412 includes a plurality of slotted apertures 444, where each aperture 444 directs a coolant flow into a valley 442 of the heat sink 430.

Figure 5A:
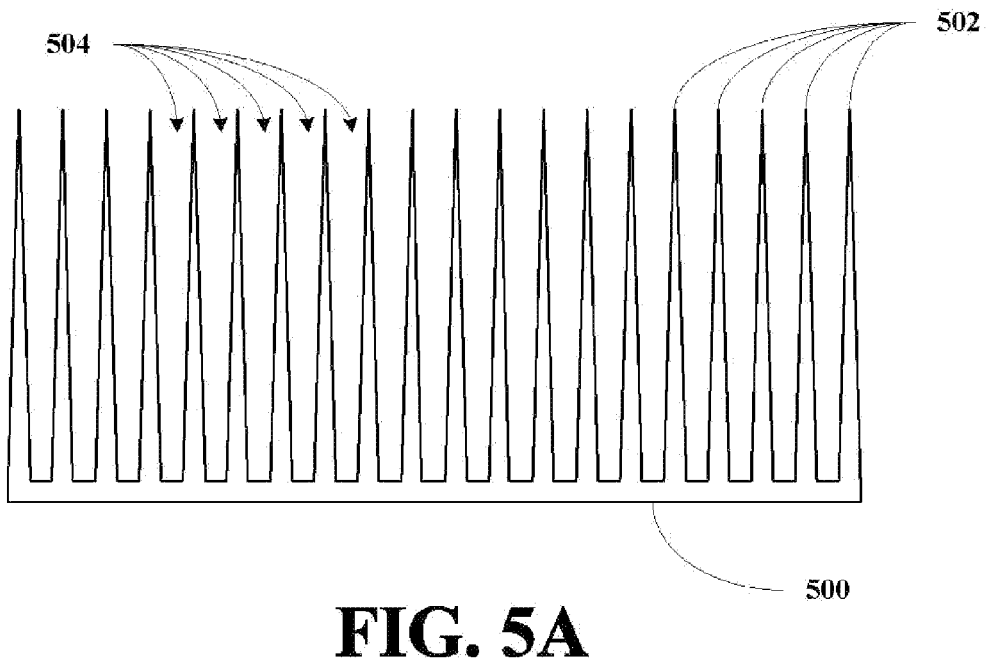
FIGS. 5A & B depict two alternate designs of radiators or heat sinks for use in the microwave ovens of this invention.

Referring now to FIG. 5A, another embodiment of a heat sink of this invention, generally 500, is shown to include tapered fins 502 and associated tapered valleys 504.

Figure 5B:
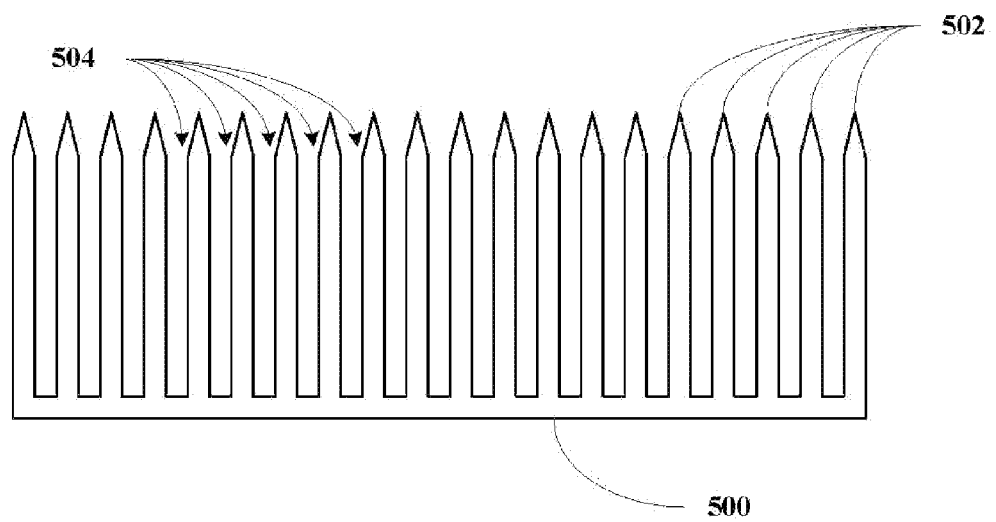

Referring now to FIG. 5B, another embodiment of a heat sink of this invention, generally 500, is shown to include triangle tipped rectangular fins 502 and associated valleys 504.

Analytical Instrument Embodiments with Radiators

Figure 6A:
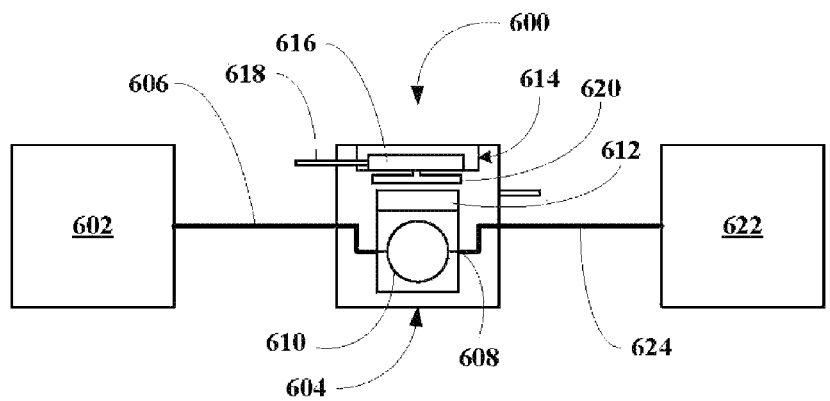
FIG. 6A depicts an analytical instrument including a microwave oven apparatus of this invention.

Referring now to FIG. 6A, an embodiment of an instrument of this invention, generally 600, is shown to include a sample supply assembly 602 and a microwave oven apparatus 604, where the sample supply assembly 602 is adapted to forward a sample to the oven apparatus 604 via sample path 606. The oven apparatus 604 includes a heating zone 608 with a chromatographic column 610 disposed inside the zone 608. The oven apparatus 604 also includes a heat sink 612 attached to a backside of the heating zone 606. The oven apparatus 604 also includes a cooling assembly 614. The cooling assembly 614 includes a vortex cooler 616, a coolant supply conduit 618 connected to a supply of coolant (not shown). The vortex cooler 616 also includes an outlet 620 adapted to direct coolant onto the heat sink 610.

The system 600 also includes a detection/analyzer assembly 622 connected to the oven apparatus 604 via a oven output path 624. The sample supply assembly 602 can be a single port injector, a automated sample injector system, a sample loop, an in-line sample loop, an automated sample loop apparatus for forwarding numerous samples to the column, or any other sample supply assembly used in analytical instruments now or will be used in the future. The detector/analyzer assembly 622 can be any now know or yet to be developed oxide detection and analyzing system including, without limitation, IR spectrometers, FTIR spectrometers, MS spectrometers, UV spectrometers, UV fluorescence spectrometers, ICR spectrometers, any other spectrographic detection and analyzing system or mixtures or combinations thereof.

Figure 6B:
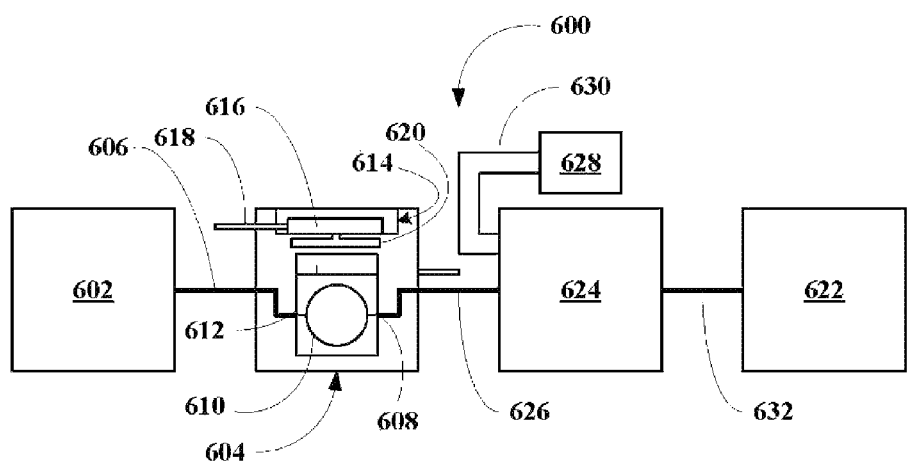
FIG. 6B depicts another analytical instrument including a microwave oven apparatus of this invention.

Referring now to FIG. 6B, another embodiment of an instrument of this invention, generally 600, is shown to include a sample supply assembly 602 and a microwave oven apparatus 604, where the sample supply assembly 602 is adapted to forward a sample to the oven apparatus 604 via sample path 606. The oven apparatus 604 includes a heating zone 608 with a chromatographic column 610 disposed inside the zone 608. The oven apparatus 604 also includes a heat sink 612 attached to a backside of the heating zone 606. The oven apparatus 604 also includes a cooling assembly 614. The cooling assembly 614 includes a vortex cooler 616, a coolant supply conduit 618 connected to a supply of coolant (not shown). The vortex cooler 616 also includes an outlet 620 adapted to direct coolant onto the heat sink 610.

The system 600 also includes an oxidation unit 624, where the oxidation unit 624 is connected to the oven apparatus 604 by an oven output path 626. The oxidation unit 624 includes an oxidizing agent supply 628 and a conduit 630 connecting the oxidizing agent supply 628 to the oxidation unit 624. The system 600 also includes a detection/analyzer assembly 622, where the assembly 622 is connected to the oxidation unit 624 via an oxidation unit output path 632. The oven output path 626 can include a mixing or nebulizing unit (not shown) immediately upstream of the oxidation or combustion unit 624 adapted to supply a thoroughly mixed sample and oxidizing agent mixture to the combustion unit 624 or an atomized sample and oxidizing agent mixture to the combustion unit 624. The sample supply assembly 602 can be a single port injector, a automated sample injector system, a sample loop, an in-line sample loop, an automated sample loop apparatus for forwarding numerous samples to the column, or any other sample supply assembly used in analytical instruments now or will be used in the future. The detector/analyzer assembly 622 can be any now know or yet to be developed oxide detection and analyzing system including, without limitation, IR spectrometers, FTIR spectrometers, MS spectrometers, UV spectrometers, UV fluorescence spectrometers, chemiluminescence spectrometers, ICR spectrometers, any other spectrographic detection and analyzing system or mixtures or combinations thereof. If the detection system includes a chemiluminescent detector, then detector will also include a source of ozone and associated conduits between the ozone generator and the detector.

Figure 6C:
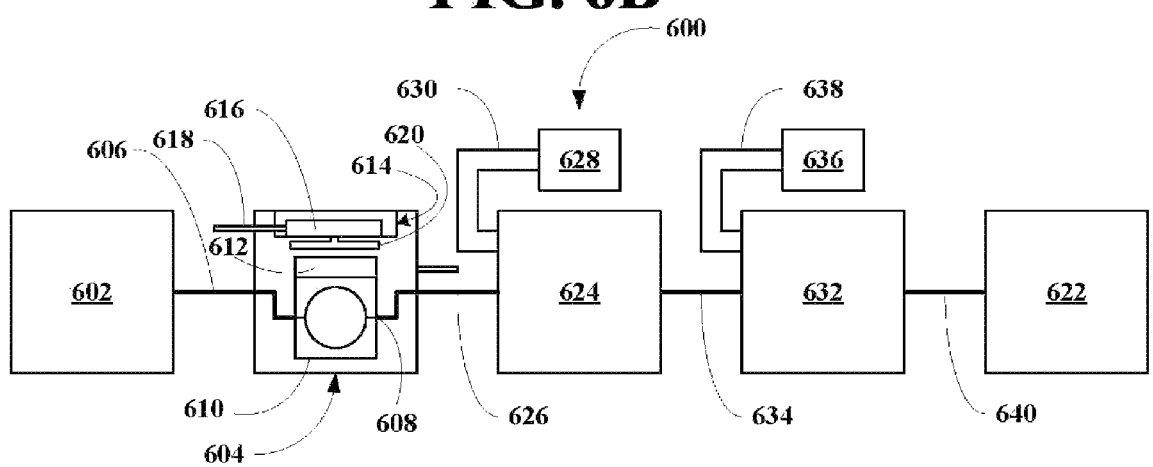
FIG. 6C depicts another analytical instrument including a microwave oven apparatus of this invention.

Referring now to FIG. 6C, another embodiment of an instrument of this invention, generally 600, is shown to include a sample supply assembly 602 and a microwave oven apparatus 604, where the sample supply assembly 602 is adapted to forward a sample to the oven apparatus 604 via sample path 606. The oven apparatus 604 includes a heating zone 608 with a chromatographic column 610 disposed inside the zone 608. The oven apparatus 604 also includes a heat sink 612 attached to a backside of the heating zone 606. The oven apparatus 604 also includes a cooling assembly 614. The cooling assembly 614 includes a vortex cooler 616, a coolant supply conduit 618 connected to a supply of coolant (not shown). The vortex cooler 616 also includes an outlet 620 adapted to direct coolant onto the heat sink 610.

The system 600 also includes an oxidation unit 624, where the oxidation unit 624 is connected to the oven apparatus 604 by an oven output path 626. The oxidation unit 624 includes an oxidizing agent supply 628 and a conduit 630 connecting the oxidizing agent supply 628 to the oxidation unit 624. The system 600 also includes a reduction unit 632, where the reduction unit 632 is connected to the oxidation unit 624 via an oxidation unit output path 634. The reduction unit 632 includes a reducing agent supply 636 and a conduit 638 connecting the reducing agent supply 636 to the reduction unit 632. The system 600 also includes a detection/analyzer assembly 622, where the assembly 622 is connected to the reduction unit 632 via a reduction unit output path 640. The oven output path 626 can include a mixing or nebulizing unit (not shown) immediately upstream of the oxidation or combustion unit 624 adapted to supply a thoroughly mixed sample and oxidizing agent mixture to the combustion unit 624 or an atomized sample and oxidizing agent mixture to the combustion unit 624. The sample supply assembly 602 can be a single port injector, a automated sample injector system, a sample loop, an in-line sample loop, an automated sample loop apparatus for forwarding numerous samples to the column, or any other sample supply assembly used in analytical instruments now or will be used in the future. The detector/analyzer assembly 614 can be any now know or yet to be developed oxide detection and analyzing system including, without limitation, IR spectrometers, FTIR spectrometers, MS spectrometers, UV spectrometers, UV fluorescence spectrometers, chemiluminescence spectrometers, ICR spectrometers, any other spectrographic detection and analyzing system or mixtures or combinations thereof. If the detection system includes a chemiluminescent detector, then detector will also include a source of ozone and associated conduits between the ozone generator and the detector.

Cooling System Embodiments with Coolant Flow Channels

Figure 7A:
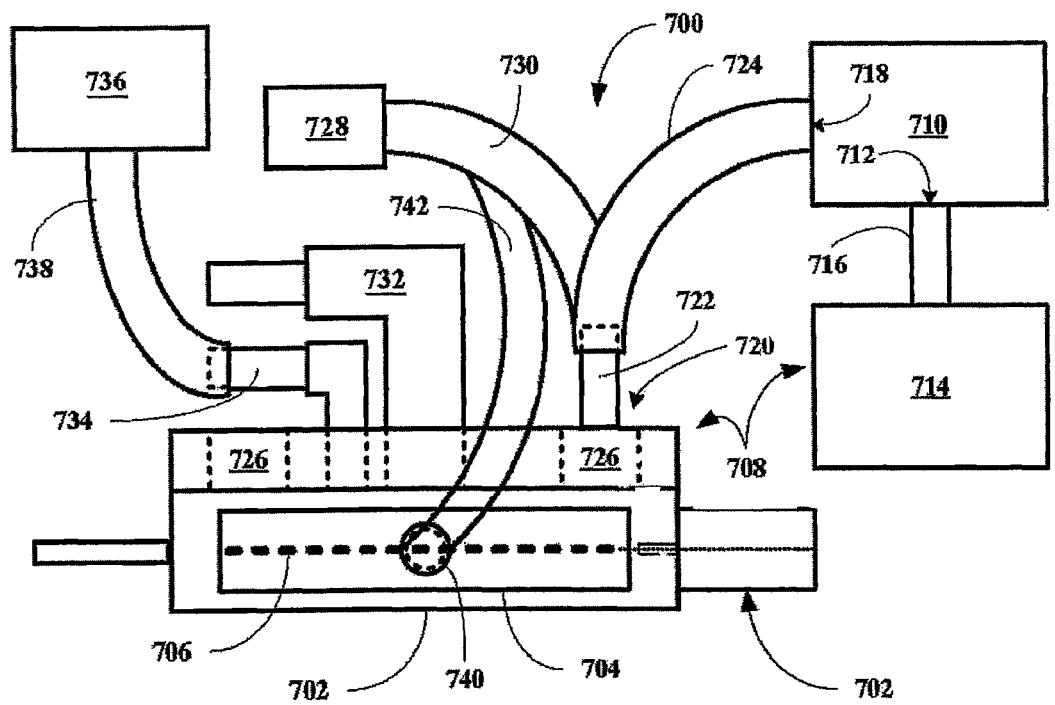
FIG. 7A depicts a top view of another embodiments of a microwave heated oven apparatus including a cooling system of this invention.

Referring now to FIG. 7A, another embodiment of a cooled microwave oven apparatus of this invention, generally 700, is shown to include a housing 702. The housing 702 includes a microwave heated zone 704 including a chromatographic column 706. The housing 702 also includes a cooling system 708. The cooling system 708 includes a vortex cooler 710 including a coolant inlet 712 connected to a coolant reservoir or a source of a coolant 714 via a conduit 716. The vortex cooler 710 also includes a cooled coolant outlet 718. The housing 702 includes a coolant chamber 720. The coolant chamber 720 including a coolant inlet 722 connected to the cooled coolant outlet 718 of the vortex cooler 710 via a cooled coolant conduit 724. The coolant chamber 720 also includes a flow channel 726 in thermal contact with the heated zone 704. The coolant chamber 720 also includes an outlet (not shown, it is hidden by the inlet 722) connected to a vent 728 via an exhaust conduit 730. The housing 702 is also shown with two transfer lines apparatuses 732 (only one shown) described herein. The apparatus 700 also includes an oven purge inlet 734 connected to an oven purge supply 736 via an oven purge supply conduit 738 and an oven purge outlet 740 connected to the vent 728 or the exhaust conduit 730 via a oven purge exhaust conduit 742.

Figure 7B:
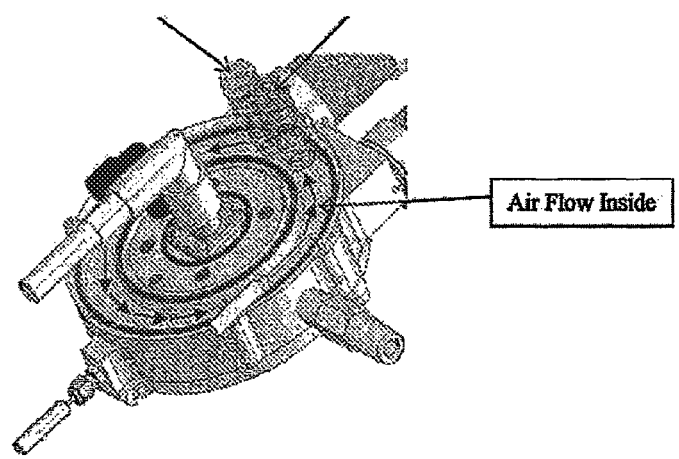
FIG. 7B depicts a front view of the heat sink of FIG. 7A.

Referring now to FIG. 7B, a 3D rendering of the apparatus of FIG. 7A is shown with corresponding parts labeled accordingly and showing the coolant flow in the channel.

Figure 7C:
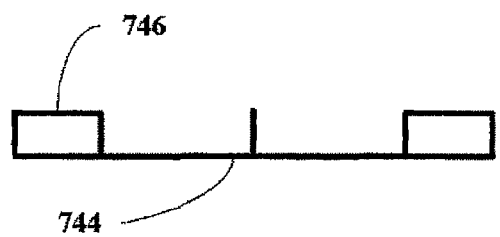
FIG. 7C is a front view of the fins contained inside of the radiator of the cooled microwave oven shown in FIG. 7A.
Figure 7D:
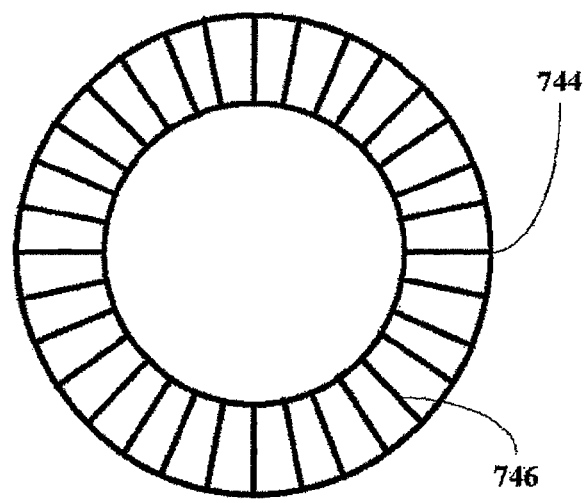
FIG. 7D is a top view of the fins shown in FIG. 7C.

Referring now to FIG. 7C, another embodiment of a cooled microwave oven apparatus of this invention, generally 700, is shown to include a housing 702. The housing 702 includes a microwave heated zone 704 including a chromatographic column 706. The housing 702 also includes a cooling system 708. The cooling system 708 includes a vortex cooler 710 including a coolant inlet 712 connected to a coolant reservoir or a source of a coolant 714 via a conduit 716. The vortex cooler 710 also includes a cooled coolant outlet 718. The housing 702 includes a coolant chamber 720. The coolant chamber 720 including a coolant inlet 722 connected to the cooled coolant outlet 718 of the vortex cooler 710 via a cooled coolant conduit 724. The coolant chamber 720 also includes a flow channel 726 in thermal contact with the heated zone 704. The coolant chamber 720 also includes an outlet (not shown, it is hidden by the inlet 722) connected to a vent 728 via an exhaust conduit 730. The housing 702 is also shown with two transfer lines apparatuses 732 (only one shown) described herein. The apparatus 700 also includes an oven purge inlet 734 connected to an oven purge supply 736 via an oven purge supply conduit 738 and an oven purge outlet 740 connected to the vent 728 or the exhaust conduit 730 via a oven purge exhaust conduit 742. The channel 726 includes a radiator 744 including fins 746. The radiator 744 with fins 746 is shown in FIGS. 7D & E.

Analytical Instrument Embodiments with Coolant Flow Channels

Figure 8A:
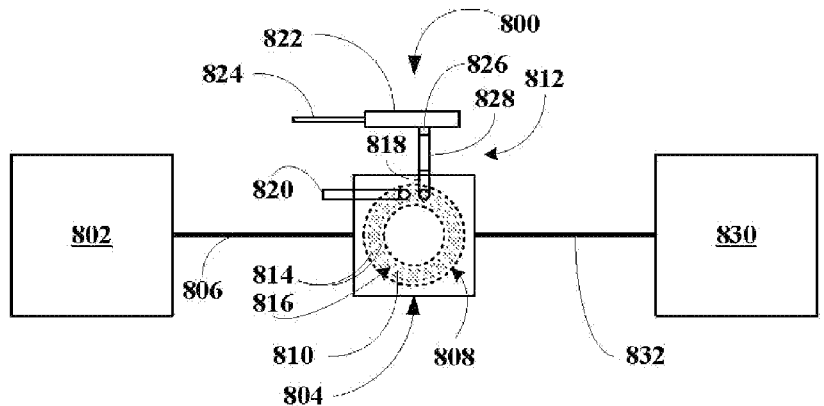
FIG. 8A depicts an analytical instrument including a microwave oven apparatus of this invention.

Referring now to FIG. 8A, an embodiment of an instrument of this invention, generally 800, is shown to include a sample supply assembly 802 and a microwave oven apparatus 804, where the sample supply assembly 802 is adapted to forward a sample to the oven apparatus 804 via sample path 806. The oven apparatus 804 includes a heating zone 808 with a chromatographic column 810 disposed inside the zone 808. The oven apparatus 804 also includes a cooling assembly 812 having a coolant chamber 814 in thermal contact with the heating zone 808. The chamber 814 includes a coolant flow channel 816 and a cooled coolant inlet 818 and a coolant exhaust output 820. The cooling assembly 812 also includes a vortex cooler 822 having a coolant inlet 824 connected to a supply of coolant (not shown). The vortex cooler 822 also includes a cooled coolant outlet 826 connected to chamber inlet 818 via a coolant conduit 828.

The system 800 also includes a detection/analyzer assembly 830 connected to the oven apparatus 804 via an oven output path 832. The sample supply assembly 802 can be a single port injector, a automated sample injector system, a sample loop, an in-line sample loop, an automated sample loop apparatus for forwarding numerous samples to the column, or any other sample supply assembly used in analytical instruments now or will be used in the future. The detector/analyzer assembly 830 can be any now know or yet to be developed oxide detection and analyzing system including, without limitation, IR spectrometers, FTIR spectrometers, MS spectrometers, UV spectrometers, UV fluorescence spectrometers, ICR spectrometers, any other spectrographic detection and analyzing system or mixtures or combinations thereof.

Figure 8B:
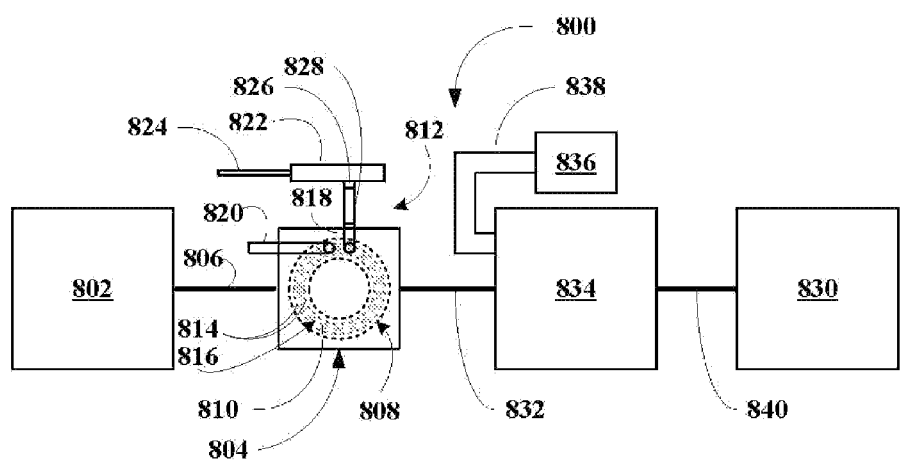
FIG. 8B depicts another analytical instrument including a microwave oven apparatus of this invention.

Referring now to FIG. 8B, another embodiment of an instrument of this invention, generally 800, is shown to include a sample supply assembly 802 and a microwave oven apparatus 804, where the sample supply assembly 802 is adapted to forward a sample to the oven apparatus 804 via sample path 806. The oven apparatus 804 includes a heating zone 808 with a chromatographic column 810 disposed inside the zone 808. The oven apparatus 804 also includes a cooling assembly 812 having a coolant chamber 814 in thermal contact with the heating zone 808. The chamber 814 includes a coolant flow channel 816 and a cooled coolant inlet 818 and a coolant exhaust output 820. The cooling assembly 812 also includes a vortex cooler 822 having a coolant inlet 824 connected to a supply of coolant (not shown). The vortex cooler 822 also includes a cooled coolant outlet 826 connected to chamber inlet 818 via a coolant conduit 828.

The system 800 also includes an oxidation unit 834, where the oxidation unit 834 is connected to the oven apparatus 804 by the oven output path 832. The oxidation unit 834 also includes an oxidizing agent supply 836 and a conduit 838 connecting the oxidizing agent supply 836 to the oxidation unit 834. The system 800 also includes a detection/analyzer assembly 830, where the assembly 830 is connected to the oxidation unit 834 via an oxidation unit output path 840. The oven output path 832 can include a mixing or nebulizing unit (not shown) immediately upstream of the oxidation or combustion unit 834 adapted to supply a thoroughly mixed sample and oxidizing agent mixture to the combustion unit 834 or an atomized sample and oxidizing agent mixture to the combustion unit 834. The sample supply assembly 802 can be a single port injector, a automated sample injector system, a sample loop, an in-line sample loop, an automated sample loop apparatus for forwarding numerous samples to the column, or any other sample supply assembly used in analytical instruments now or will be used in the future. The detector/analyzer assembly 830 can be any now know or yet to be developed oxide detection and analyzing system including, without limitation, IR spectrometers, FTIR spectrometers, MS spectrometers, UV spectrometers, UV fluorescence spectrometers, chemiluminescence spectrometers, ICR spectrometers, any other spectrographic detection and analyzing system or mixtures or combinations thereof. If the detection system includes a chemiluminescent detector, then detector will also include a source of ozone and associated conduits between the ozone generator and the detector.

Figure 8C:
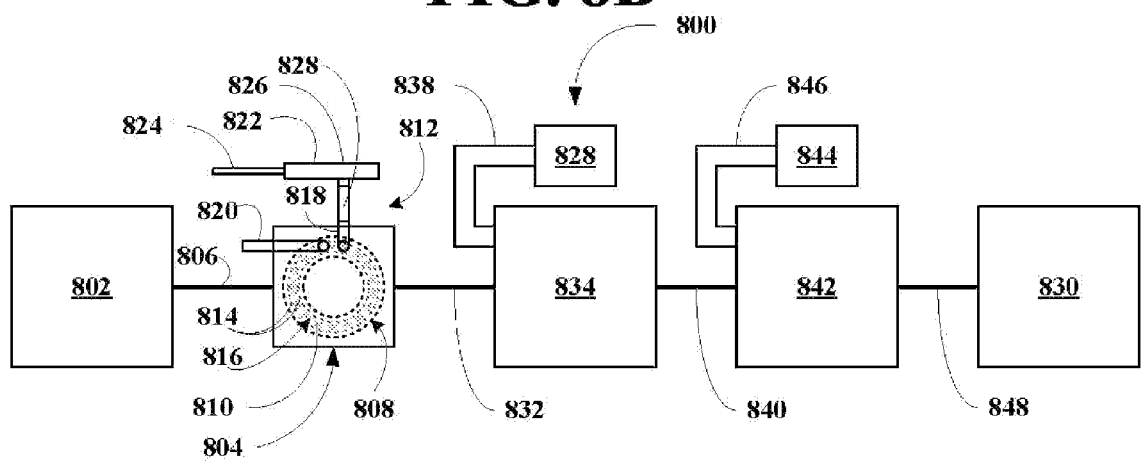
FIG. 8C depicts another analytical instrument including a microwave oven apparatus of this invention.

Referring now to FIG. 8C, another embodiment of an instrument of this invention, generally 800, is shown to include a sample supply assembly 802 and a microwave oven apparatus 804, where the sample supply assembly 802 is adapted to forward a sample to the oven apparatus 804 via sample path 806. The oven apparatus 804 includes a heating zone 808 with a chromatographic column 810 disposed inside the zone 808. The oven apparatus 804 also includes a cooling assembly 812 having a coolant chamber 814 in thermal contact with the heating zone 808. The chamber 814 includes a coolant flow channel 816 and a cooled coolant inlet 818 and a coolant exhaust output 820. The cooling assembly 812 also includes a vortex cooler 822 having a coolant inlet 824 connected to a supply of coolant (not shown). The vortex cooler 822 also includes a cooled coolant outlet 826 connected to chamber inlet 818 via a coolant conduit 828.

The system 800 also includes the oxidation unit 834, where the oxidation unit 834 is connected to the oven apparatus 804 by the oven output path 832. The oxidation unit 834 also includes the oxidizing agent supply 836 and the conduit 838 connecting the oxidizing agent supply 836 to the oxidation unit 834. The system 800 also includes a reduction unit 842, where the reduction unit 842 is connected to the oxidation unit 834 via the oxidation unit output path 840. The reduction unit 842 includes a reducing agent supply 844 and a conduit 846 connecting the reducing agent supply 844 to the reduction unit 842. The system 800 also includes a detection/analyzer assembly 830, where the assembly 830 is connected to the reduction unit 842 via a reduction unit output path 848. The oven output path 832 can include a mixing or nebulizing unit (not shown) immediately upstream of the oxidation or combustion unit 834 adapted to supply a thoroughly mixed sample and oxidizing agent mixture to the combustion unit 834 or an atomized sample and oxidizing agent mixture to the combustion unit 834. The sample supply assembly 802 can be a single port injector, a automated sample injector system, a sample loop, an in-line sample loop, an automated sample loop apparatus for forwarding numerous samples to the column, or any other sample supply assembly used in analytical instruments now or will be used in the future. The detector/analyzer assembly 830 can be any now know or yet to be developed oxide detection and analyzing system including, without limitation, IR spectrometers, FTIR spectrometers, MS spectrometers, UV spectrometers, UV fluorescence spectrometers, chemiluminescence spectrometers, ICR spectrometers, any other spectrographic detection and analyzing system or mixtures or combinations thereof. If the detection system includes a chemiluminescent detector, then detector will also include a source of ozone and associated conduits between the ozone generator and the detector.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:
1. A radiant energy heated oven apparatus comprising:
a radiant energy heated oven including:
a heated zone,
a closed-loop assembly with a coolant supply reservoir,
a coolant chamber in thermal contact with the radiant energy heated oven including:
a coolant inlet via a conduit from said coolant supply reservoir and
a coolant outlet where spent coolant is returned to the coolant supply reservoir,
where the coolant inlet directs a coolant into the chamber, the coolant absorbs thermal energy from the oven and the outlet directs spent coolant out of the chamber, cooling the oven to a desired temperature, at a desired rate or at a controlled rate,
wherein the radiant energy is microwave energy, radio wave energy or some other radiant energy capable of heating the heating zone;
a chromatography column disposed within the heating zone of the oven,
where the oven is adapted to heat the column to a desired temperature at a desired rate or to heat the column according to a temperature programmed heating profile;
and wherein the apparatus is adapted to decrease a sample cycled time of an analytical instrument including the apparatus.

2. A chromatography instrument apparatus comprising:
a sample delivery assembly,
a radiant energy heated oven apparatus for comprising:
a radiant energy heated oven including:
a heated zone,
a coolant chamber in thermal contact with the radiant energy heated oven including:
a coolant inlet and
a coolant outlet,
wherein the coolant inlet directs a coolant into the chamber, the coolant absorbs thermal energy from the oven and the outlet directs spent coolant out of the member, cooling the oven to a desired temperature, at a desired rate or at a controlled rate and
a detector/analyzer assembly;
oxidation subassemblies and/or reduction subassemblies adapted to produce detectable oxidized species and/or detectable reduced species.

3. The apparatus of claim 2, wherein the radiant energy is microwave energy, radiowave energy or any other radiant energy capable of heating the heated zone.

4. The apparatus of claim 2, further comprising:
a coolant supply reservoir and
a conduit connecting the supply reservoir to the coolant inlet of the chamber.

5. A radiant energy heated oven apparatus comprising:
a radiant energy heated oven including:
a heated zone,
a closed-loop assembly with a coolant supply reservoir,
a coolant chamber in thermal contact with the radiant energy heated oven including:
a coolant inlet via a conduit from said coolant supply reservoir and
a coolant outlet where spent coolant is returned to the coolant supply reservoir,
where the coolant inlet directs a coolant into the chamber, the coolant absorbs thermal energy from the oven and the outlet directs spent coolant out of the chamber, cooling the oven to a desired temperature, at a desired rate or at a controlled rate,
wherein the cooling chamber further includes a radiator adapted to increase thermal energy absorption by the coolant.

6. The apparatus of claim 5, wherein the radiator includes fins adapted to further increase thermal energy absorption by the coolant.

7. A radiant energy heated oven apparatus comprising:
a radiant energy heated oven including:
a heated zone,
a closed-loop assembly with a coolant supply reservoir,
a coolant chamber in thermal contact with the radiant energy heated oven including:
a coolant inlet via a conduit from said coolant supply reservoir and
a coolant outlet where spent coolant is returned to the coolant supply reservoir,
where the coolant inlet directs a coolant into the chamber, the coolant absorbs thermal energy from the oven and the outlet directs spent coolant out of the chamber, cooling the oven to a desired temperature, at a desired rate or at a controlled rate,
the cooling chamber comprising a flow channel associated with a top or a bottom of the oven, where the channel is adapted to increase thermal energy absorption by the coolant.

8. The apparatus of claim 7, wherein the channel includes a radiator adapted to further increase thermal energy absorption by the coolant.

9. The apparatus of claim 8, wherein the radiator includes fins adapted to still further increase thermal energy absorption by the coolant.

10. A chromatography instrument apparatus comprising:
a sample delivery assembly,
a radiant energy heated oven apparatus comprising:
a radiant energy heated oven including:
a heated zone,
a closed-loop coolant assembly with a coolant supply reservoir,
a coolant chamber in thermal contact with the radiant energy heated oven including:
a coolant inlet for receiving a coolant via an inlet conduit from said coolant supply reservoir, and
a coolant outlet for returning said coolant via an outlet conduit to said coolant supply or reservoir,
wherein the coolant inlet directs a coolant into the chamber, the coolant absorbs thermal energy from the oven and the outlet directs spent coolant out of the member, cooling the oven to a desired temperature, at a desired rate or at a controlled rate, and
a detector/analyzer assembly,
a chromatography column disposed within the heating zone of the oven,
where the oven is a adapted to heat the column to a desired temperature at a desired rate or to heat the column to a temperature programmed heating profile, and
wherein the apparatus is adapted to decrease a sample cycle time of an analytical instrument including the apparatus.

11. The apparatus of claim 10, wherein the cooling chamber further includes a radiator adapted to increase thermal energy absorption by the coolant.

12. The apparatus of claim 11, wherein the radiator includes fins adapted to further increase thermal energy absorption by the coolant.

13. A chromatography instrument apparatus comprising:
a sample delivery assembly,
a radiant energy heated oven apparatus comprising:
a radiant energy heated oven including:
a heated zone,
a closed-loop coolant assembly with a coolant supply reservoir,
a coolant chamber in thermal contact with the radiant energy heated oven including:
a coolant inlet for receiving a coolant via an inlet conduit from said coolant supply reservoir, and
a coolant outlet for returning said coolant via an outlet conduit to said coolant supply or reservoir,
wherein the coolant inlet directs a coolant into the chamber, the coolant absorbs thermal energy from the oven and the outlet directs spent coolant out of the member, cooling the oven to a desired temperature, at a desired rate or at a controlled rate, and a detector/analyzer assembly,
said coolant chamber comprises a flow channel associated with a top or bottom of the oven, where the channel is adapted to increase thermal energy absorption by the coolant.

14. The apparatus of claim 13, wherein the channel includes a radiator adapted to further increase thermal energy absorption by the coolant.

15. The apparatus of claim 14, wherein the radiator includes fins adapted to still further increase thermal energy absorption by the coolant.

16. The apparatus of claim 13, wherein the coolant comprises a gas, liquid or mixtures or combinations thereof.

17. The apparatus of claim 16, wherein the gaseous coolants are selected from the group consisting of air, He, Ne, Ar, Xe, Kr, oxygen, nitrogen, $CO_2$, CO, ammonia, hydrocarbons, and mixtures or combinations thereof.

18. The apparatus of claim 17, wherein the hydrocarbons are selected from the group consisting of methane, ethane, propane, butane, and mixtures or combinations thereof.

19. The apparatus of claim 16, wherein the liquid coolants are selected from the group consisting of water, $CO_2$, liquid nitrogen, chlorocarbons, fluorochlorocarbons and other refrigerants, and mixtures or combinations thereof.

20. A method for performing a chromatographic analyses comprising the steps of:
providing an instrument apparatus of claim 13,
injecting a sample from the sample delivery system into the chromatographic column in the heated zone of the oven apparatus,
subjecting the column to a temperature profile adapted to achieve a desire sample component separation,
oxidizing the sample components in an oxidation subassembly to produce detectable oxides, and
forwarding the separated sample components to the detector/analyzer assembly for detection and quantitation.

21. The method of claim 20, further comprising the step of:
prior to the forwarding step, reducing the sample components in a reduction subassembly to produce reduced detectable species.

22. The method of claim 20, further comprising the step of:
prior to the forwarding step, oxidizing the sample components in an oxidation subassembly to produce detectable oxides, and
reducing the sample components in a reduction subassembly to produce reduced detectable species.

23. The method of claim 20, wherein the temperature profile comprises a start temperature, a final temperature, at least one temperature ramp for changing the temperature from the start temperature to the final temperature.

24. The method of claim 20, wherein the temperature profile further comprises at least one temperature hold.

25. The method of claim 20, wherein the temperature ramps are positive, negative or a combination thereof.

* * * * *